US012741059B2

(12) United States Patent
Matsusaki et al.

(10) Patent No.: US 12,741,059 B2
(45) Date of Patent: Sep. 22, 2026

(54) METHOD FOR CONTROLLING YOUNG'S MODULUS OF THREE-DIMENSIONAL TISSUE BODY, METHOD FOR PRODUCING THREE-DIMENSIONAL TISSUE BODY, AND THREE-DIMENSIONAL TISSUE BODY

(71) Applicants: OSAKA UNIVERSITY, Osaka (JP); TOPPAN Holdings Inc., Tokyo (JP)

(72) Inventors: Michiya Matsusaki, Suita (JP); Naoko Sasaki, Suita (JP); Shiro Kitano, Tokyo (JP); Shinji Irie, Tokyo (JP)

(73) Assignees: OSAKA UNIVERSITY, Osaka (JP); TOPPAN HOLDINGS INC., Tokyo (JP)

( * ) Notice: Subject to any disclaimer, the term of this patent is extended or adjusted under 35 U.S.C. 154(b) by 965 days.

(21) Appl. No.: 17/908,283

(22) PCT Filed: Mar. 4, 2021

(86) PCT No.: PCT/JP2021/008449

§ 371 (c)(1),
(2) Date: Aug. 31, 2022

(87) PCT Pub. No.: WO2021/177407

PCT Pub. Date: Sep. 10, 2021

(65) Prior Publication Data

US 2023/0110381 A1 Apr. 13, 2023

(30) Foreign Application Priority Data

Mar. 5, 2020 (JP) ................................ 2020-037700

(51) Int. Cl.

| | |
|---|---|
| ***A61L 27/50*** | (2006.01) |
| ***A61L 27/24*** | (2006.01) |
| ***A61L 27/36*** | (2006.01) |
| ***A61L 27/38*** | (2006.01) |
| ***C12N 5/00*** | (2006.01) |

(52) U.S. Cl.
CPC ............... *A61L 27/50* (2013.01); *A61L 27/24* (2013.01); *A61L 27/3633* (2013.01); *A61L 27/3695* (2013.01); *A61L 27/38* (2013.01); *C12N 5/0062* (2013.01); *C12N 2513/00* (2013.01); *C12N 2533/54* (2013.01)

(58) Field of Classification Search
CPC .. A61L 27/24; A61L 27/3633; A61L 27/3695; C12N 2513/00; C12N 2533/54
See application file for complete search history.

(56) References Cited

U.S. PATENT DOCUMENTS

2007/0269476 A1 11/2007 Voytik-Harbin et al.

FOREIGN PATENT DOCUMENTS

| | | | |
|---|---|---|---|
| JP | 2012-126681 | A | 7/2012 |
| WO | WO 2010/048281 | A1 | 4/2010 |
| WO | WO 2015/072164 | A1 | 5/2015 |
| WO | WO 2016/027853 | A1 | 2/2016 |
| WO | WO 2018/143286 | A1 | 8/2018 |
| WO | WO 2019/045105 | A1 | 3/2019 |
| WO | WO 2019/189786 | A1 | 10/2019 |

OTHER PUBLICATIONS

Machine translation from PE2E Search of Matsusaki et al (WO 2018143286 A1, Published Aug. 9, 2018 (Year: 2018).*

Machine translation from PE2E Search of Shunji et al (JP 2012126681 A1, Published Jul. 5, 2012 (Year: 2012).*

Narayan et al (Colloids and Surfaces B: Biointerfaces 163 (2018) 291-300) (Year: 2018).*

International Preliminary Report on Patentability (Form/IB/373); mailed Sep. 6, 2022 in corresponding PCT Application No. PCT/JP2021/008449 (1 page).

Notification of Transmittal of Translation of the International Preliminary Report on Patentability (Form/IB/338); mailed Sep. 6, 2022 in corresponding PCT Application No. PCT/JP2021/008449 (1 page).

International Preliminary Report on Patentability (IPRP) (Form PCT/IB/373); issued Sep. 6, 2022 and Written Opinion of the International Searching Authority (Form PCT/ISA/237); mailed May 25, 2021 in corresponding PCT Application No. PCT/JP2021/008449 (5 pages) (5 pages English Translation).

Eileen Gentleman et al., "Mechanical characterization of collagen fibers and scaffolds for tissue engineering", Biomaterials, Elsevier, Amsterdam, NL, vol. 24, No. 21, Sep. 1, 2003, p. 3805-p. 3813, XP004431161.

Cevat Erisken at al., "Scaffold Fiber Diameter Regulates Human Tendon Fibroblast Growth and Differentiation", Tissue Engineering, Part A, vol. 19, No. 3-4, 2012-11-13, p. 519-p. 528, XP093123952.

Sakiko Enomoto et al., "One-step microfibers and their applications to cell cultivation", 2015 International Syposium On Micro-Nanomechatronics and Human Science(MHS), IEEE, Nov. 23, 2015, p. 1-p. 4, XP032885476.

Extended European Search Report issued in counterpart European Application No. 21765021.7 dated Feb. 6, 2024.

Gui Li et al., "Construction and application of engineered three-dimensional tumour model", The chemistry of life 36(6), 2016, p. 823 p. 833.

Komeda, Misaki, Matsusaki, Michiya, "Construction of three-dimensional interstitial tissue with high concentration extracellular matrix and capillary network by collagen microfiber", Polymer preprints, 2017, vol. 66, No. 2, #2Q10; (4 pages) (3 pages English Translation).

Matsusaki, Michiya, Komeda, Misaki, "Construction of 3D-connective tissue having high density ECM through sedimentation culture in which collagen microfiber is used", Polymer preprints, 2017, vol. 66, No. 2, #3N02; (3 pages) (4 pages English Translation).

International Search Report (Form PCT/ISA/210); mailed May 25, 2021. In corresponding PCT Application No. PCT/JP2021/008449 (4 pages) (3 pages English Translation).

* cited by examiner

*Primary Examiner* — Emily A Cordas
*Assistant Examiner* — Matasha Dhar
(74) *Attorney, Agent, or Firm* — XSENSUS LLP

(57) ABSTRACT

Disclosed is a method for controlling the Young's modulus of a three-dimensional tissue containing cells and an extracellular matrix by adjusting the average diameter of an extracellular matrix in production of the three-dimensional tissue.

7 Claims, 5 Drawing Sheets

METHOD FOR CONTROLLING YOUNG'S MODULUS OF THREE-DIMENSIONAL TISSUE BODY, METHOD FOR PRODUCING THREE-DIMENSIONAL TISSUE BODY, AND THREE-DIMENSIONAL TISSUE BODY

CROSS REFERENCE TO RELATED APPLICATIONS

This application is a U.S. national stage of International Application No. PCT/JP2021/008449, filed on Mar. 4, 2021, which claims the priority benefit of Japanese Application No. 2020-037700, filed on Mar. 5, 2020. Both the International Application and the Japanese Application are incorporated by reference herein in their entirety.

TECHNICAL FIELD

The present invention relates to a method for controlling the Young's modulus of a three-dimensional tissue, a method for producing a three-dimensional tissue, and a three-dimensional tissue.

BACKGROUND ART

Techniques to construct three-dimensional tissue bodies of cells ex vivo have been developed in recent years. Use of a highly biocompatible scaffold material is preferred in producing a tissue imitating biological tissue. The present inventors have previously proposed a method for producing a three-dimensional tissue, comprising three-dimensionally disposing cells each coated with a coating containing collagen to form a three-dimensional tissue (Patent Literature 1), and a method for producing a three-dimensional tissue, comprising: forming coated cells with a coating formed on the surface of each cell; and three-dimensionally disposing the coated cells, wherein the forming coated cells includes soaking cells in a liquid containing a coating component and separating the soaked cells and the liquid containing a coating component from each other with a liquid-permeable membrane (Patent Literature 2), and the like. In addition, the present inventors have proposed a method for producing a three-dimensional tissue having a higher collagen concentration than conventional ones, the method involving use of homogenized collagen (Patent Literature 3).

CITATION LIST

Patent Literature

Patent Literature 1: International Publication No. WO 2015/072164
Patent Literature 2: International Publication No. WO 2016/027853
Patent Literature 3: International Publication No. WO 2018/143286

SUMMARY OF INVENTION

Technical Problem

Actual in vivo tissues are known to differ in tissue "hardness" across in vivo sites and lesions. For example, cancer tissues are known to be harder than normal tissues as a tendency. The hardness of tissue may serve as a factor for the characteristics of an organ or pathological condition, and hence it is important in producing a tissue imitating biological tissue to reproduce the original hardness.

However, there are currently no reports on a method of adjusting the hardness of a tissue to be produced with use of a highly biocompatible scaffold material to give a desired hardness according to a tissue of interest to be reproduced. For example, a method of controlling a growing environment for cells to harden by culturing the cells in polyacrylamide gel is known (R. W. Tilghman et al., PLoS One, 5(9) e12905 (2010).), but the polyacrylamide gel is not a substance present in living bodies and thus not preferred from the viewpoint of imitation of biological tissue.

In view of this, an object of one aspect of the preset invention is to provide a method for controlling the Young's modulus of a three-dimensional tissue in the three-dimensional tissue to be produced with use of a highly biocompatible scaffold material. An object of another aspect of the present invention is to provide a method for producing a three-dimensional tissue having a desired Young's modulus. An object of still another aspect of the present invention is to provide a three-dimensional tissue having a Young's modulus of 20 kPa or more.

Solution to Problem

The present inventors compared a composition containing an extracellular matrix of small average diameter in an aqueous medium and a composition containing an extracellular matrix of large average diameter in an aqueous medium, wherein the concentrations of the extracellular matrices are identical, to find that the composition containing an extracellular matrix of small average diameter exhibits a higher Young's modulus.

Accordingly, the present invention relates to, for example, the followings.

[1] A method for controlling the Young's modulus of a three-dimensional tissue containing cells and an extracellular matrix by adjusting the average diameter of the extracellular matrix.

[2] The method according to [1], wherein the extracellular matrix is a polypeptide having an RGD sequence.

[3] The method according to [2], wherein the extracellular matrix is a biocompatible material with molecules identical to biomolecules.

[4] The method according to any one of [1] to [3], wherein the extracellular matrix contains an exogenous fragmented extracellular matrix.

[5] The method according to any one of [1] to [4], wherein the extracellular matrix contains collagen.

[6] The method according to any one of [1] to [5], comprising adjusting the average diameter of the extracellular matrix to 20 nm or more and 1000 nm or less.

[7] The method according to any one of [1] to [6], comprising adjusting the three-dimensional tissue to contain fragmented extracellular matrices having different average diameters.

[8] The method according to [7], comprising adjusting to give an extracellular matrix having an average diameter of 20 nm or more and 1000 nm or less and an extracellular matrix having an average diameter of 1.5 μm or more and 8.5 μm or less.

[9] The method according to [8], wherein the extracellular matrix having an average diameter of 20 nm or more and 1000 nm or less and the extracellular matrix having an average diameter of 1.5 μm or more and 8.5 μm or less are used at a ratio of 1:100 to 100:1 in terms of weight.

[10] The method according to [9], wherein the extracellular matrix having an average diameter of 20 nm or more and 1000 nm or less is more used than the extracellular matrix having an average diameter of 1.5 μm or more and 8.5 μm or less in terms of weight.

[11] The method according to any one of [1] to [10], wherein the Young's modulus of the three-dimensional tissue is 20 kPa to 250 kPa.

[12] A method for producing a three-dimensional tissue, comprising:

a step of providing an extracellular matrix subjected to adjustment of average diameter according to a desired Young's modulus for the three-dimensional tissue;

a step of obtaining a cell suspension by mixing the extracellular matrix and cells in an aqueous medium; and a step of incubating the cell suspension.

[13] The method according to [12], wherein the extracellular matrix is a polypeptide having an RGD sequence.

[14] The method according to [13], wherein the extracellular matrix is a biocompatible material with molecules identical to biomolecules.

[15] The method according to any one of [12] to [14], wherein the extracellular matrix contains an exogenous fragmented extracellular matrix.

[16] The method according to any one of [12] to [15], wherein the extracellular matrix contains collagen.

[17] The method according to any one of [12] to [16], wherein the extracellular matrix subjected to adjustment of average diameter contains an extracellular matrix having an average diameter of 20 nm or more and 1000 nm or less.

[18] The method according to any one of [12] to [17], wherein the step of providing a fragmented extracellular matrix includes adjusting the three-dimensional tissue to contain fragmented extracellular matrices having different average diameters.

[19] The method according to [18], comprising adjusting the three-dimensional tissue to contain a fragmented extracellular matrix having an average diameter of 20 nm or more and 1000 nm or less and a fragmented extracellular matrix having an average diameter of 1.5 μm or more and 8.5 μm or less.

[20] The method according to any one of [12] to [19], further comprising a step of accumulating the cells and the extracellular matrix by applying external force to the cell suspension between the step of obtaining a cell suspension and the step of incubating the cell suspension.

[21] The method according to any one of [12] to [20], wherein the Young's modulus of the three-dimensional tissue is 20 kPa to 250 kPa.

[22] A three-dimensional tissue, comprising:

cells; and an extracellular matrix having an average diameter of 20 nm or more and 1000 nm or less, wherein the fragmented extracellular matrix is disposed among the cells, the extracellular matrix is a biocompatible material with molecules identical to biomolecules, and the three-dimensional tissue has a Young's modulus of 20 kPa or more.

[23] The three-dimensional tissue according to [22], wherein the extracellular matrix is a polypeptide having an RGD sequence.

[24] The three-dimensional tissue according to [22] or [23], wherein the extracellular matrix contains an exogenous fragmented extracellular matrix.

[25] The three-dimensional tissue according to any one of [19] to [24], wherein the content percentage of the extracellular matrix having an average diameter of 20 nm or more and 1000 nm or less is 5% by weight or more and 90% by weight or less on the basis of the total weight of the three-dimensional tissue.

[26] The three-dimensional tissue according to any one of [19] to [25], further comprising an extracellular matrix having an average diameter of 1.5 μm or more and 8.5 μm or less.

[27] A forming agent for a three-dimensional tissue, comprising:

an extracellular matrix having an average diameter of 20 nm or more and 1000 nm or less; and an aqueous medium, wherein the Young's modulus of the three-dimensional tissue is 20 kPa or more.

In addition, the present invention relates to, for example, the followings.

[1] A method for controlling the Young's modulus of a three-dimensional tissue containing cells and an extracellular matrix by adjusting the average diameter of a fragmented extracellular matrix in production of a three-dimensional tissue.

[2] The method according to [1], further comprising adjusting the content of the fragmented extracellular matrix.

[3] The method according to [1] or [2], wherein the fragmented extracellular matrix is a polypeptide having an RGD sequence.

[4] The method according to [3], wherein the fragmented extracellular matrix is a biocompatible material with molecules identical to biomolecules.

[5] The method according to any one of [1] to [4], wherein the fragmented extracellular matrix contains collagen.

[6] The method according to any one of [1] to [5], comprising adjusting the average diameter of the fragmented extracellular matrix to 20 nm or more and 1000 nm or less.

[7] The method according to any one of [1] to [5], wherein the adjusting the average diameter of the fragmented extracellular matrix includes adjusting the three-dimensional tissue to contain fragmented extracellular matrices having different average diameters.

[8] The method according to [7], further comprising adjusting the contents of the fragmented extracellular matrices having different average diameters in the three-dimensional tissue.

[9] The method according to [8], wherein the adjusting the three-dimensional tissue to contain fragmented extracellular matrices having different average diameters and the adjusting the contents of the fragmented extracellular matrices having different average diameters in the three-dimensional tissue include:

increasing the Young's modulus of the three-dimensional tissue by increasing the content of a fragmented extracellular matrix of small average diameter in the three-dimensional tissue, or decreasing the Young's modulus of the three-dimensional tissue by decreasing the content of a fragmented extracellular matrix of small average diameter in the three-dimensional tissue.

[10] The method according to any one of [7] to [9], wherein the fragmented extracellular matrices having different average diameters include a fragmented extracellular matrix having an average diameter of 1000 nm or less and a fragmented extracellular matrix having an average diameter of more than 1000 nm.

[11] The method according to any one of [7] to [9], wherein the fragmented extracellular matrices having different average diameters include a fragmented extracellular matrix having an average diameter of 20 nm or more and 1000 nm or less and a fragmented extracellular matrix having an average diameter of 1.5 μm or more and 8.5 μm or less.

[12] The method according to any one of [8] to [11], wherein a fragmented extracellular matrix of smaller average diameter and a fragmented extracellular matrix of larger average diameter are used at a ratio of 1:100 to 100:1 in terms of weight.

[13] The method according to any one of [1] to [12], wherein the Young's modulus of the three-dimensional tissue is 20 kPa to 250 kPa.

[14] A method for producing a three-dimensional tissue, comprising:

a step of providing a fragmented extracellular matrix subjected to adjustment of average diameter according to a desired Young's modulus for the three-dimensional tissue;

a step of obtaining a cell suspension by mixing the extracellular matrix and cells in an aqueous medium; and a step of incubating the cell suspension.

[15] The method according to [14], wherein the step of providing a fragmented extracellular matrix is a step of providing a fragmented extracellular matrix subjected to adjustment of average diameter and content according to a desired Young's modulus for the three-dimensional tissue.

[16] The method according to [14] or [15], wherein the fragmented extracellular matrix is a polypeptide having an RGD sequence.

[17] The method according to [16], wherein the fragmented extracellular matrix is a biocompatible material with molecules identical to biomolecules.

[18] The method according to any one of [14] to [17], wherein the fragmented extracellular matrix contains collagen.

[19] The method according to any one of [14] to [18], wherein the fragmented extracellular matrix subjected to adjustment of average diameter contains a fragmented extracellular matrix having an average diameter of 20 nm or more and 1000 nm or less.

[20] The method according to any one of [14] to [19], wherein the step of providing a fragmented extracellular matrix includes adjusting the three-dimensional tissue to contain fragmented extracellular matrices having different average diameters.

[21] The method according to [20], further comprising adjusting the contents of the fragmented extracellular matrices having different average diameters in the three-dimensional tissue.

[22] The method according to [21], wherein the adjusting the three-dimensional tissue to contain fragmented extracellular matrices having different average diameters and the adjusting the contents of the fragmented extracellular matrices having different average diameters in the three-dimensional tissue include:

increasing the Young's modulus of the three-dimensional tissue by increasing the content of a fragmented extracellular matrix of small average diameter in the three-dimensional tissue, or decreasing the Young's modulus of the three-dimensional tissue by decreasing the content of a fragmented extracellular matrix of small average diameter in the three-dimensional tissue.

[23] The method according to any one of [20] to [22], wherein the fragmented extracellular matrices having different average diameters include a fragmented extracellular matrix having an average diameter of 1000 nm or less and a fragmented extracellular matrix having an average diameter of more than 1000 nm.

[24] The method according to any one of [20] to [23], wherein the fragmented extracellular matrices having different average diameters include a fragmented extracellular matrix having an average diameter of 20 nm or more and 1000 nm or less and a fragmented extracellular matrix having an average diameter of 1.5 μm or more and 8.5 μm or less.

[25] The method according to any one of [21] to [24], wherein a fragmented extracellular matrix of smaller average diameter and a fragmented extracellular matrix of larger average diameter are used at a ratio of 1:100 to 100:1 in terms of weight.

[26] The method according to any one of [14] to [25], wherein the Young's modulus of the three-dimensional tissue is 20 kPa to 250 kPa.

[27] A three-dimensional tissue, comprising:

cells; and a fragmented extracellular matrix having an average diameter of 20 nm or more and 1000 nm or less, wherein the fragmented extracellular matrix is disposed among the cells, the fragmented extracellular matrix is a biocompatible material with molecules identical to biomolecules, and the three-dimensional tissue has a Young's modulus of 20 kPa or more.

[28] The three-dimensional tissue according to [27], wherein the fragmented extracellular matrix is a polypeptide having an RGD sequence.

[29] The three-dimensional tissue according to [27] or [28], wherein the content percentage of the fragmented extracellular matrix having an average diameter of 20 nm or more and 1000 nm or less is 5% by weight or more and 90% by weight or less on the basis of the total weight of the three-dimensional tissue.

[30] The three-dimensional tissue according to any one of [27] to [29], further comprising a fragmented extracellular matrix having an average diameter of more than 1000 nm.

[31] The three-dimensional tissue according to any one of [27] to [29], further comprising a fragmented extracellular matrix having an average diameter of 1.5 μm or more and 8.5 μm or less.

[32] The three-dimensional tissue according to any one of [27] to [31], wherein the ratio between a fragmented extracellular matrix of smaller average diameter and a fragmented extracellular matrix of larger average dimeter in the three-dimensional tissue is 1:100 to 100:1 in terms of weight.

[33] The three-dimensional tissue according to any one of [27] to [32], having a Young's modulus of 20 kPa to 250 kPa.

Advantageous Effects of Invention

According to the present invention, a method for controlling the Young's modulus of a three-dimensional tissue, which is a three-dimensional tissue to be produced with use of a highly biocompatible scaffold material, can be provided. Thereby, a method for producing a three-dimensional tissue having a desired Young's modulus can be provided. According to the present invention, a three-dimensional tissue having a Young's modulus of 20 kPa or more can be provided.

According to the present invention, a three-dimensional tissue having a desired Young's modulus can be obtained, and hence enables production of various tissue models having Young's modulus close to those in living bodies, and use thereof for evaluation of and screening or the like for drugs. In addition, according to the present invention, a three-dimensional tissue having a high Young's modulus can be obtained, which is currently difficult to produce with use of a highly biocompatible scaffold material, and hence enables production of a cancer tissue model that exhibits a high Young's modulus in living bodies and use thereof for evaluation of and screening or the like for drugs.

DESCRIPTION OF EMBODIMENTS

Figure 1:
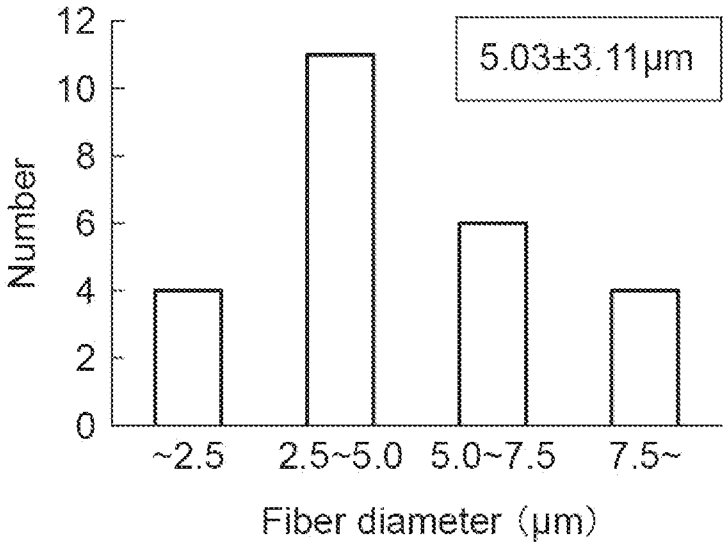
FIG. 1 shows a graph representing the fiber diameter distribution of fragmented collagen in a collagen dispersion in Example 2.

Hereinafter, embodiments for implementing the present invention will be described in detail. However, the present invention is not limited to the following embodiments.

<Method for Controlling Young's Modulus of Three-Dimensional Tissue>

The method according to the present embodiment controls the Young's modulus of a three-dimensional tissue containing cells and an extracellular matrix by adjusting the average diameter of the extracellular matrix.

In the present specification, the term "three-dimensional tissue" means a cell assemblage in which cells are three-dimensionally disposed via an extracellular matrix, wherein the assemblage is artificially made through cell culture. Accordingly, the three-dimensional tissue contains cells and an extracellular matrix. The extracellular matrix may be disposed among at least some of the cells. There may be a part in which cells are in direct contact with each other in the three-dimensional tissue. It is preferable that the three-dimensional tissue be a three-dimensional tissue in which cells and an extracellular matrix are three-dimensionally distributed and the extracellular matrix is disposed among cells, and it is more preferable that the three-dimensional tissue be a three-dimensional tissue in which cells and an extracellular matrix are three-dimensionally distributed in a homogeneous manner and the extracellular matrix is disposed among cells. The shape of the three-dimensional tissue is not particularly limited, and examples thereof include a sheet-like shape, a spherical shape, a nearly spherical shape, an ellipsoidal shape, a nearly ellipsoidal shape, a hemispherical shape, a nearly hemispherical shape, a semicircular shape, a nearly semicircular shape, a rectangular parallelepiped shape, a nearly rectangular parallelepiped, and the like. Generally speaking, biological tissue includes blood vessels, sweat glands, lymphatic vessels, sebaceous glands, and so on, and the structure is more complex than those of three-dimensional tissue bodies. Thus, the three-dimensional tissue is readily distinguishable from biological tissue. The three-dimensional tissue may be a massive assembly adhering to a support, or a massive assembly not adhering to a support.

The cells may be somatic cells or germ cells. Moreover, the cells may be stem cells, or cultured cells such as primary cultured cells, subcultured cells, and cell line cells. In the present specification, the term "stem cell" means a cell having self-replication competence and pluripotency. Stem cells include pluripotent stem cells, which have an ability to differentiate into any cell type, and tissue stem cells (also called somatic stem cells), which have an ability to differentiate into a specific cell type. Examples of pluripotent stem cells include embryonic stem cells (ES cells), somatic nuclear transfer ES cells (ntES cells), and induced pluripotent stem cells (iPS cells). Examples of tissue stem cells include mesenchymal stem cells (e.g., bone marrow-derived stem cells), hematopoietic stem cells, and neural stem cells.

The cells constituting the three-dimensional tissue may include one or more types of cells. Examples of the cells include mesenchymal cells such as fibroblasts (e.g., normal human dermal fibroblasts (NHDF), normal human cardiac fibroblasts (NHCF), and human gingival fibroblasts (HGF)), chondrocytes, and osteoblasts, vascular endothelial cells (e.g., human umbilical vein endothelial cells (HUVEC)), cancer cells such as colon cancer cells (e.g., human colon cancer cells (HT29)) and liver cancer cells, cardiomyocytes (e.g., human iPS cell-derived cardiomyocytes (iPS-CM)), epithelial cells (e.g., human gingival epithelial cells), keratinocytes, lymphatic endothelial cells, neurons, hepatocytes, tissue stem cells, embryonic stem cells, induced pluripotent stem cells, adherent cells (e.g., immunocytes), and smooth muscle cells (e.g., aortic smooth muscle cells (Aorta-SMC)).

The total number of the cells constituting the three-dimensional tissue according to the present embodiment is not particularly limited, and appropriately determined in view of the thickness and shape of the three-dimensional tissue to be constructed, the size of a cell culture vessel to be used for the construction, and others.

The extracellular matrix is a material to fill gaps among at least some of the cells in the three-dimensional tissue. The extracellular matrix may be an extracellular matrix molecule assemblage formed of a plurality of extracellular matrix molecules. The extracellular matrix molecules may be those of a substance present outside cells in an organism. It is preferable that the extracellular matrix be a biocompatible material with molecules identical to biomolecules. Any substance can be used for the extracellular matrix molecules, unless the growth of cells and the formation of a cell assemblage are adversely affected. Examples of the extracellular matrix molecules include, but are not limited to, collagen, laminin, fibronectin, vitronectin, elastin, tenascin, entactin, fibrillin, proteoglycan, and the like. For the extracellular matrix, one of them may be used singly, and a combination of them may be used. For example, the extracellular matrix may contain collagen, or be collagen. If the extracellular matrix is collagen, the collagen functions as a scaffold for cell adhesion, promoting the formation of a three-dimensional cell construct to a much higher degree. It is preferable that the extracellular matrix in the present embodiment be a substance present outside animal cells, that is, an animal extracellular matrix. In addition, the extracellular matrix molecule may be a modified product or variant of the above-described extracellular matrix molecule or a polypeptide such as a chemically synthesized peptide, unless the growth of cells and the formation of a cell assemblage are adversely affected.

The extracellular matrix may have repeats of a sequence represented as Gly-X-Y, which is characteristic to collagen. Here, Gly represents a glycine residue, and X and Y each independently represent any amino acid residue. The multiple repeats of Gly-X-Y each may be identical or different. Inclusion of repeats of the sequence represented as Gly-X-Y reduces constraint on the disposition of molecular chains, giving much superior functions as a scaffold material. In the extracellular matrix having repeats of the sequence represented as Gly-X-Y, the proportion of the sequence represented as Gly-X-Y may be 80% or more, and is preferably 95% or more to the entire amino acid sequence. The extracellular matrix may be a polypeptide having an RGD sequence. The RGD sequence refers to a sequence represented as Arg-Gly-Asp (arginine residue-glycine residue-aspartic acid residue). If the extracellular matrix has the RGD sequence, the cell adhesion is much more promoted, and the extracellular matrix is much more preferable as a scaffold material. Extracellular matrices containing the sequence represented as Gly-X-Y and the RGD sequence include collagen, fibronectin, vitronectin, laminin, cadherin and the like.

Examples of collagen include fibrillar collagen and nonfibrillar collagen. The term fibrillar collagen means collagen that serves as a primary component of collagen fiber, and specific examples thereof include type I collagen, type II collagen, and type III collagen. Examples of nonfibrillar collagen include type IV collagen.

Examples of proteoglycan include, but are not limited to, chondroitin sulfate proteoglycan, heparan sulfate proteoglycan, keratan sulfate proteoglycan, and dermatan sulfate proteoglycan.

The extracellular matrix may contain at least one selected from the group consisting of collagen, laminin, and fibronectin, and it is preferable that the extracellular matrix contains collagen. The collagen is preferably fibrillar collagen, and more preferably type I collagen. Commercially available collagen may be used for the fibrillar collagen, and specific examples thereof include porcine skin-derived type I collagen manufactured by NH Foods Ltd. and porcine skin-derived type I and type III collagen manufactured by the same company. If mixed collagen of multiple types such as the type I and type III collagen is used for the collagen, collagen of single type may be separated by purification for use. For example, a collagen of desired type can be exclusively obtained in such a manner that a salt is added to a solution containing mixed collagen of multiple types, collagens of multiple types are separated from each other through centrifugation, and a precipitate or supernatant is collected. The collagen of desired type obtained can be further removed of the salt by dialysis, and may be further freeze-dried after dialysis.

The extracellular matrix may be an animal-derived extracellular matrix. Examples of the animal species from which the extracellular matrix is derived include, but are not limited to, a human, a pig, a bovine, and the like. For the extracellular matrix, a component derived from one animal species may be used, and components derived from a plurality of animal species may be used in combination. The animal species from which the extracellular matrix is derived may be the same as or different from the origin of the cells for three-dimensional tissue formation.

Examples of the shape of the extracellular matrix include a fibrous shape. The term fibrous shape means a shape constituted of a filamentous extracellular matrix, or a shape constituted by intermolecular crosslinking of a filamentous extracellular matrix. At least part of the extracellular matrix may be fibrous. The shape of the extracellular matrix is the shape of a lump of the extracellular matrix (an assemblage of the extracellular matrix) to be observed in microscopy, and the extracellular matrix preferably has a size described later in terms of average diameter and/or average length. Fibrous extracellular matrices include thin filamentous products formed by the assemblage of a plurality of filamentous extracellular matrix molecules (fibrils), filamentous products formed by the additional assemblage of fibrils, and products formed by defibering such a filamentous product. If an extracellular matrix whose shape is fibrous is contained, the RGD sequence is conserved without being broken in the fibrous extracellular matrix, and the extracellular matrix can much more effectively function as a scaffold material for cell adhesion.

The term "fragmenting" means making the size of an assemblage of the extracellular matrix smaller. The extracellular matrix subjected to fragmentation (also referred to as "fragmented extracellular matrix") may contain an extracellular matrix subjected to defibering. The extracellular matrix subjected to defibering is a defibered product obtained by applying physical force to the above-described extracellular matrix. For example, defibering is performed under conditions not allowing cleavage of bonds in the extracellular matrix molecules.

The fragmented extracellular matrix may at least partly contain an extracellular matrix subjected to defibering. The fragmented extracellular matrix may consist only of an extracellular matrix subjected to defibering. That is, the fragmented extracellular matrix may be an extracellular matrix subjected to defibering. It is preferable that the extracellular matrix subjected to defibering contain collagen subjected to defibering (defibered collagen). It is preferable that the defibered collagen be maintaining the triple helix structure derived from collagen. The defibered collagen may be a component partially maintaining the triple helix structure derived from collagen. Dispersing the fragmented collagen in an aqueous medium can allow the fragmented collagen to readily come into contact with cells in the aqueous medium, promoting the formation of the three-dimensional tissue.

The average length of the fragmented extracellular matrix may be 100 nm or more and 400 μm or less, or 100 nm or more and 200 μm or less. In an embodiment, from the viewpoint of facilitating formation of thick tissue, the average length of the fragmented extracellular matrix may be 5 μm or more and 400 μm or less, or 10 μm or more and 400 μm or less, or 22 μm or more and 400 μm or less, or 100 μm or more and 400 μm or less. In another embodiment, from the viewpoints of facilitating stabilization of tissue formation and achieving more superior redispersibility, the average length of the fragmented extracellular matrix may be 100 μm or less, or 50 μm or less, or 30 μm or less, or 15 μm or less, or 10 μm or less, or 1 μm or less, and 100 nm or more. It is preferable that the average length of most part of the whole fragmented extracellular matrix be within the numerical range. Specifically, it is preferable that the average length of 95% of the whole fragmented extracellular matrix be within the numerical range. It is preferable that the fragmented extracellular matrix be fragmented collagen whose average length is within the range, and it is more preferable that the fragmented extracellular matrix be defibered collagen whose average length is within the range.

The average diameter of the fragmented extracellular matrix may be, for example, 20 nm or more and 30 μm or less, or 20 nm or more and 10 μm or less. In the method of the present embodiment, the Young's modulus of the three-dimensional tissue can be increased by decreasing the average diameter of the fragmented extracellular matrix contained in the three-dimensional tissue; conversely, the Young's modulus of the three-dimensional tissue can be decreased by increasing the average diameter. Accordingly, the method of the present embodiment may include adjusting the average diameter of the extracellular matrix to any of average diameters shown as examples in the following.

A fragmented extracellular matrix whose average diameter is in the order of nanometers (1000 nm or less) is also referred to as nanofiber (NF). The average diameter of the nanofiber may be, for example, 20 nm or more and 1000 nm or less, or 20 nm or more and 500 nm or less, or 20 nm or more and 200 nm or less, or 40 nm or more and 130 nm or less, or 20 nm or more and 100 nm or less. A fragmented extracellular matrix whose average diameter is in the order of micrometers (more than 1000 nm) is also referred to as microfiber (MF). The average diameter of the microfiber may be, for example, more than 1 μm and 30 μm or less, or more than 1 μm and 30 μm or less, or more than 1 μm and 10 μm or less, or 1.5 μm or more and 8.5 μm or less, or 2 μm or more and 8.5 μm or less. The shapes of the nanofiber and microfiber in the present embodiment are, for example, not required to be fibrous for the above-described fragmented extracellular matrix.

The method of the present embodiment may include adjusting the fragmented extracellular matrix contained in the three-dimensional tissue totally into nanofiber or microfiber. The method of the present embodiment may include adjusting the three-dimensional tissue to contain fragmented extracellular matrices having different average diameters. For example, the three-dimensional tissue may be adjusted to contain both the aforementioned nanofiber and microfiber; specifically, the three-dimensional tissue may be adjusted, for example, to contain a fragmented extracellular matrix of 20 nm or more and 1000 nm or less and a fragmented extracellular matrix having an average diameter of 1.5 μm or more and 8.5 μm or less. The three-dimensional tissue may be adjusted to contain nanofibers having different average diameters; specifically, the three-dimensional tissue may be adjusted, for example, to contain a fragmented extracellular matrix of 20 nm or more and 100 nm or less and a fragmented extracellular matrix of more than 100 nm and 200 nm or less. A desired Young's modulus can be imparted to the three-dimensional tissue by adjusting the ratio of the fragmented extracellular matrices having different average diameters in terms of their weights. For example, the fragmented extracellular matrix of smaller average diameter (e.g., nanofiber) and the fragmented extracellular matrix of larger average diameter (e.g., microfiber) may be used at a ratio of 1:100 to 100:1, or at a ratio of 1:10 to 10:1, or at a ratio of 1:3 to 3:1, or at a ratio of 1:2 to 2:1, in terms of weight. Specifically, for example, a fragmented extracellular matrix having an average diameter of 20 nm or more and 1000 nm or less and a fragmented extracellular matrix having an average diameter of 1.5 μm or more and 8.5 μm or less can be used at a ratio of 1:100 to 100:1 in terms of weight. The fragmented extracellular matrix of smaller average diameter (e.g., nanofiber) may be used more than the fragmented extracellular matrices of larger average diameter (e.g., microfiber) in terms of weight. Specifically, for example, a fragmented extracellular matrix having an average diameter of 20 nm or more and 1000 nm or less may be used more than a fragmented extracellular matrix having an average diameter of 1.5 μm or more and 8.5 μm or less in terms of weight.

The content percentage of the whole fragmented extracellular matrix in the three-dimensional tissue may be, for example, 0.33% by mass or more, 0.5% by mass or more, 1% by mass or more, 2% by mass or more, or 5% by weight or more, on the basis of the total mass of the fragmented extracellular matrix and the cells. The content of the fragmented extracellular matrix in the three-dimensional tissue may be 90% by mass or less, 80% by mass or less, 70% by mass or less, 60% by mass or less, 50% by mass or less, 40% by mass or less, 30% by mass or less, 20% by mass or less, 15% by mass or less, 10% by mass or less, 5% by mass or less, or 1% by mass or less, on the basis of the total mass of the extracellular matrix subjected to fragmentation and the cells. The content of the fragmented extracellular matrix in the three-dimensional tissue may be, for example, 0.33% by mass or more and 90% by mass or less, or 0.5% by mass or more and 90% by mass or less, or 1.0% by mass or more and 90% by mass or less, or 5% by weight or more and 90% by weight or less, or 5% by weight or more and 40% by weight or less, on the basis of the total mass of the extracellular matrix subjected to fragmentation and the cells. In the method of the present embodiment, the Young's modulus of the three-dimensional tissue may be controlled by adjusting the average diameter and content percentage of the fragmented extracellular matrix. Accordingly, the method of the present embodiment may further include adjusting the contents of fragmented extracellular matrices having different average diameters in the three-dimensional tissue. For example, the Young's modulus of the three-dimensional tissue can be increased by increasing the content of the fragmented extracellular matrix of small average diameter in the three-dimensional tissue or decreasing the content of the fragmented extracellular matrix of large average diameter in the three-dimensional tissue. Conversely, the Young's modulus of the three-dimensional tissue can be decreased by decreasing the content of the fragmented extracellular matrix of small average diameter in the three-dimensional tissue or increasing the content of the fragmented extracellular matrix of large average diameter in the three-dimensional tissue. That is, adjusting the three-dimensional tissue to contain fragmented extracellular matrices having different average diameters and adjusting the contents of the fragmented extracellular matrices having different average diameters in the three-dimensional tissue may include increasing the Young's modulus of the three-dimensional tissue by increasing the content of the fragmented extracellular matrix of small average diameter in the three-dimensional tissue (or by decreasing the content of the fragmented extracellular matrix of large average diameter in the three-dimensional tissue), or decreasing the Young's modulus of the three-dimensional tissue by decreasing the content of the fragmented extracellular matrix of small average diameter in the three-dimensional tissue (or by increasing the content of the fragmented extracellular matrix of large average diameter in the three-dimensional tissue).

The aforementioned ranges of average length and average diameter are those optimized from the viewpoint of tissue formation, and it is thus desired that each average length or average diameter fall within the corresponding range shown above in application to tissue formation.

The average lengths and average diameters of fragmented extracellular matrices can be determined through measurement with an optical microscope and image analysis for individual fragmented extracellular matrices. In the present specification, the term "average length" means the mean of lengths in the longitudinal direction in a measurement sample, and the term "average diameter" means the mean of lengths in the direction perpendicular to the longitudinal direction in a measurement sample.

The method of fragmenting an extracellular matrix is not limited, and fragmentation may be performed by application of physical force. In contrast to extracellular matrices subjected to enzymatic treatment, the molecular structure of an extracellular matrix fragmented by application of physical force is typically consistent with that before fragmentation (the molecular structure is maintained). The method of fragmenting an extracellular matrix may be, for example, a method of finely crushing a massive extracellular matrix. An extracellular matrix may be fragmented with a solid phase, or fragmented in an aqueous medium. For example, an extracellular matrix may be fragmented by application of physical force such as an ultrasonic homogenizer, a stirring homogenizer, and a high-pressure homogenizer. If a stirring homogenizer is used, an extracellular matrix may be directly homogenized, or homogenized in an aqueous medium such as physiological saline. The average diameter of a fragmented extracellular matrix can be adjusted, for example, by adjusting the time or number of cycles of homogenization. Examples of methods for producing a fragmented extracellular matrix, in particular, having a small average diameter in the order of nanometers (1000 nm or less) include homogenizing a dispersion containing an extracellular matrix (e.g., collagen) obtained by dispersing it in an aqueous medium and then optionally incubating in an aqueous medium at 10 °C or less (e.g., 4 °C±1 °C). Examples of the homogenization include homogenizing with a homogenizer, stirring, and applying pressure, and stirring may be performed with a stirrer. Each aqueous medium may be pure water, or an aqueous solution such as a phosphate-containing aqueous solution (e.g., PBS buffer). The time of incubation at 10 °C or less (e.g., 4 °C±1 °C) after the homogenization is, for example, 6 hours or more, 12 hours or more, 24 hours or more, 48 hours or more, or 72 hours or more. The aqueous medium in the homogenization (first aqueous medium) and the aqueous medium in the incubation (second aqueous medium) may be identical or different. Each aqueous medium may contain a salt or not.

If an extracellular matrix is fragmented in an aqueous medium, an extracellular matrix subjected to fragmentation can be produced, for example, with a method including: a step of fragmenting an extracellular matrix in an aqueous medium; and a step of removing the aqueous medium from the liquid containing the extracellular matrix subjected to fragmentation and the aqueous medium (removal step). The removal step may be performed, for example, by a freeze-drying method. The phrase "removing an aqueous medium" does not mean that moisture attaching to the extracellular matrix component subjected to fragmentation is completely absent, but that attaching moisture is absent to a degree normally achievable by the aforementioned common drying technique.

At least part of the fragmented extracellular matrix may be intermolecularly or intramolecularly crosslinked. The extracellular matrix subjected to fragmentation may be crosslinked within the molecules constituting the extracellular matrix subjected to fragmentation, or crosslinked among the molecules constituting the extracellular matrix subjected to fragmentation.

Examples of crosslinking methods include methods of physical crosslinking by application of heat, ultraviolet rays, radiation, or the like, and methods of chemical crosslinking by a crosslinking agent, enzymatic reaction, or the like, but the methods are not particularly limited. The crosslinking (physical crosslinking and chemical crosslinking) may be crosslinking via covalent bonds.

In fragmented collagen, crosslinking may be formed among collagen molecules (triple helix structure), or formed among collagen fibrils formed by collagen molecules. The crosslinking may be crosslinking by heat (thermal crosslinking). Thermal crosslinking can be performed, for example, by heat treatment under reduced pressure with use of a vacuum pump. If thermal crosslinking of collagen molecules is performed, defibered collagen may be crosslinked through peptide bonds (—NH—CO—) each formed by an amino group of a collagen molecule with a carboxy group of the same or another collagen molecule.

Alternatively, the fragmented extracellular matrix can be crosslinked with use of a crosslinking agent. The crosslinking agent may be, for example, one capable of crosslinking a carboxyl group and an amino group, or one capable of crosslinking amino groups. For example, aldehyde-based, carbodiimide-based, epoxide-based, and imidazole-based crosslinking agents are preferable as the crosslinking agent from the viewpoints of economic efficiency, safety, and operability, and specific examples thereof include glutaraldehyde and water-soluble carbodiimide such as 1-ethyl-3-(3-dimethylaminopropyl)carbodiimide hydrochloride and 1-cyclohexyl-3-(2-morpholinyl-4-ethyl)carbodiimide sulfonate.

In quantitation of degree of crosslinking, an appropriate degree of crosslinking can be selected, for example, according to the type of the fragmented extracellular matrix and the means for crosslinking. The degree of crosslinking may be 1% or more, 2% or more, 4% or more, 8% or more, or 12% or more, and may be 30% or less, 20% or less, or 15% or less.

If amino groups in extracellular matrix molecules are used for crosslinking, the degree of crosslinking can be quantitated on the basis of a TNBS method described, for example, in Non Patent Literature 2. The degree of crosslinking determined with the TNBS method may be within the aforementioned range. The degree of crosslinking determined with the TNBS method is the proportion of amino groups used for crosslinking among the amino groups possessed by an extracellular matrix.

The degree of crosslinking may be calculated by quantitating carboxyl groups. In the case of a water-insoluble extracellular matrix, for example, quantitation may be performed with a TBO (toluidine blue O) method. The degree of crosslinking determined with the TBO method may be within the aforementioned range.

The content of the extracellular matrix in the three-dimensional tissue may be 0.01% by mass or more, 0.05% by mass or more, 0.1% by mass or more, 0.5% by mass or more, 1% by mass or more, 2% by mass or more, 3% by mass or more, 4% by mass or more, 5% by mass or more, 6% by mass or more, 7% by mass or more, 8% by mass or more, 9% by mass or more, 10% by mass, 15% by mass or more, 20% by mass or more, 25% by mass or more, or 30% by mass or more, and may be 90% by mass or less, 80% by mass or less, 70% by mass or less, 60% by mass or less, 50% by mass or less, 30% by mass or less, 20% by mass or less, or 15% by mass or less, on the basis of the dry weight of the three-dimensional tissue. The content of the extracellular matrix in the three-dimensional tissue may be 0.01 to 90% by mass, or 10 to 90% by mass, 10 to 80% by mass, 10 to 70% by mass, 10 to 60% by mass, 1 to 50% by mass, 10 to 50% by mass, 10 to 30% by mass, or 20 to 30% by mass, on the basis of the dry weight of the three-dimensional tissue.

Here, the phrase "the extracellular matrix in the three-dimensional tissue" means an extracellular matrix constituting the three-dimensional tissue, which may be derived from an endogenous extracellular matrix or derived from an exogenous extracellular matrix.

The term "endogenous extracellular matrix" means an extracellular matrix which extracellular matrix-producing cells produce. Examples of extracellular matrix-producing cells include the aforementioned mesenchymal cells such as fibroblasts, chondrocytes, and osteoblasts. The endogenous extracellular matrix may be fibrillar or nonfibrillar.

The term "exogenous extracellular matrix" means an extracellular matrix to be externally supplied. The three-dimensional tissue according to the present embodiment contains an extracellular matrix that is an exogenous extracellular matrix and has been subjected to fragmentation. The animal species from which the exogenous extracellular matrix is derived may be the same as or different from that from which the endogenous extracellular matrix is derived. Examples of the animal species to serve as the origin include a human, a pig, and a bovine. The exogenous extracellular matrix may be an artificial extracellular matrix.

If the extracellular matrix is collagen, the exogenous extracellular matrix is also referred to as "exogenous collagen", and "exogenous collagen", the term meaning collagen to be externally supplied, is a collagen molecule assemblage formed of a plurality of collagen molecules, and specific examples thereof include fibrillar collagen and nonfibrillar collagen. It is preferable that the exogenous collagen be fibrillar collagen. The term fibrillar collagen means collagen that serves as a primary component of collagen fiber, and examples of fibrillar collagen include type I collagen, type II collagen, and type III collagen. Commercially available collagen may be used for the fibrillar collagen, and specific examples thereof include porcine skin-derived type I collagen manufactured by NH Foods Ltd. Examples of exogenous nonfibrillar collagen include type IV collagen.

The animal species from which the exogenous extracellular matrix is derived may be different from that from which the cells are derived. If the cells include extracellular matrix-producing cells, the animal species from which the exogenous extracellular matrix is derived may be different from that from which the extracellular matrix-producing cells are derived. In other words, the exogenous extracellular matrix may be a xenogeneic extracellular matrix.

That is, if the three-dimensional tissue contains an endogenous extracellular matrix and an extracellular matrix subjected to fragmentation, the above content percentage of the extracellular matrix constituting the three-dimensional tissue indicates the total amount of the endogenous extracellular matrix and the extracellular matrix subjected to fragmentation. The content percentage of the extracellular matrix can be calculated from the volume of the three-dimensional tissue obtained and the mass of the three-dimensional tissue subjected to decellularization.

For example, in the case that the extracellular matrix contained in the three-dimensional tissue is collagen, the methods for quantitating the collagen content of the three-dimensional tissue include, for example, a method of quantitating hydroxyproline as shown in the following. A lysate obtained by lysing the three-dimensional tissue is mixed with hydrochloric acid (HCl) and incubated at high temperature for a specific period of time, the temperature is then returned to room temperature, and supernatant obtained by centrifugation is diluted to a specific concentration to prepare a sample. Hydroxyproline standard solution is treated in the same manner as for the sample, and then serially diluted to prepare standards. Each of the sample and the standards are subjected to specific treatment with hydroxyproline assay buffer and a detection reagent, and the absorbance at 570 nm is measured. The absorbance of the sample is compared with those of the standards to calculate the collagen content. Alternatively, a lysate obtained by directly suspending the three-dimensional tissue in hydrochloric acid of high concentration to lyse it is centrifuged to collect the supernatant, which may be used for quantitation of the collagen component. The three-dimensional tissue to be lysed may be in a state as collected from culture solution, or the three-dimensional tissue may be subjected to drying treatment after being collected and lysed with the liquid component removed. However, if the three-dimensional tissue in a state as collected from culture solution is lysed and subjected to quantitation of the collagen component, measurements of the weight of the three-dimensional tissue are expected to vary because of the influence of components of a culture medium which the three-dimensional tissue has absorbed and a residual culture medium due to a problem lying in experimental procedures, and hence it is preferable from the viewpoint of stable measurement of the weight of the tissue and the collagen content per unit weight to employ the weight after drying as a reference.

More specific examples of methods for quantitating the collagen content include the following method.

(Preparation of Sample)

The whole of a three-dimensional tissue subjected to freeze-drying treatment is mixed with 6 mol/L HCl and incubated with a heat block at 95 °C for 20 hours or more, and the temperature is then returned to room temperature. After centrifugation at 13000 g for 10 minutes, the supernatant of the sample solution is collected. Dilution is appropriately performed with 6 mol/L HCl so that results in measurement described later can fall within the range of a calibration curve, and a 200-μL portion is diluted with 100 μL of ultrapure water to prepare a sample. A 35-μL portion of the sample is used.

(Preparation of Standards)

Into a screwcap tube, 125 μL of standard solution (1200 μg/mL in acetic acid) and 125 μL of 12 mol/1 HCl are added, mixed together, and incubated with a heat block at 95 °C for 20 hours, and the temperature is then returned to room temperature. After centrifugation at 13000 g for 10 minutes, the supernatant is diluted with ultrapure water to produce S1 of 300 μg/mL, and S1 is serially diluted to produce S2 (200 μg/mL), S3 (100 μg/mL), S4 (50 μg/mL), S5 (25 μg/mL), S6 (12.5 μg/mL), and S7 (6.25 μg/mL). Additionally, S8 (0 μg/mL), which consists only of 90 μL of 4 mol/1 HCl, is prepared.

(Assay)

The standards and the sample each in a volume of 35 μL are added into a plate (attached to a QuickZyme Total Collagen Assay kit, QuickZyme Biosciences). Into each well, 75 μL of assay buffer (attached to the kit) is added. The plate is enclosed with a seal, and incubated at room temperature with shaking for 20 minutes. The seal is removed, and 75 μL of a detection reagent (reagent A:B=30 μL:45 μL, attached to the kit) is added to each well. The plate is enclosed with a seal, and the solutions are mixed by shaking and incubated at 60 °C for 60 minutes. The plate is sufficiently cooled on ice, the seal is removed, and absorbance at 570 nm is measured. The absorbance of the sample is compared with those of the standards to calculate the collagen content.

The collagen occupying the three-dimensional tissue may be specified with the area ratio or volume ratio. The phrase "specifying with the area ratio or volume ratio" means, for example, that after making the collagen in the three-dimensional tissue distinguishable from other tissue constituents by a known staining technique (e.g., immunostaining using an anti-collagen antibody, or Masson's trichrome staining) or the like, the proportion of regions in which collagen is present to the entire three-dimensional tissue is calculated by means of visual observation, any microscope, image analysis software, or the like. In specifying with the area ratio, which cross-section or surface in the three-dimensional tissue is used for specifying the area ratio is not limited; for example, in the case that the three-dimensional tissue is a spherical body, the area ratio may be specified with a cross-sectional view passing through its generally center part.

If the collagen in the three-dimensional tissue is specified with the area ratio, for example, the area percentage is 0.01 to 99%, and it is preferable that the area percentage be 1 to 99%, it is preferable that the area percentage be 5 to 90%, it is preferable that the area percentage be 7 to 90%, it is preferable that the area percentage be 20 to 90%, and it is more preferable that the area percentage be 50 to 90%, based on the total area of the three-dimensional tissue. The "collagen in the three-dimensional tissue" is as described above. The area percentage of the collagen constituting the three-dimensional tissue indicates the total area percentage of endogenous collagen and exogenous collagen. The area percentage of collagen can be calculated as the ratio of the area of collagen stained blue in Masson's trichrome staining for the three-dimensional tissue obtained to the total area of a cross-section passing through a generally center part of the three-dimensional tissue.

It is preferable that the remaining percentage of the three-dimensional tissue after trypsin treatment at a trypsin concentration of 0.25%, a temperature of 37 °C, and pH 7.4 for a reaction time of 15 minutes be 70% or more, it is more preferable that the remaining rate of the three-dimensional tissue after trypsin treatment at a trypsin concentration of 0.25%, a temperature of 37 °C, and pH 7.4 for a reaction time of 15 minutes be 80% or more, and it is even more preferable that the remaining rate of the three-dimensional tissue after trypsin treatment at a trypsin concentration of 0.25%, a temperature of 37 °C, and pH 7.4 for a reaction time of 15 minutes be 90% or more. Such a three-dimensional tissue is less likely to undergo decomposition by an enzyme in culture or after culture, thus being stable. The remaining percentage can be calculated, for example, from the mass of the three-dimensional tissue before and after trypsin treatment.

The remaining percentage of the three-dimensional tissue after collagenase treatment at a collagenase concentration of 0.25%, a temperature of 37 °C, and pH 7.4 for a reaction time of 15 minutes may be 70% or more, it is more preferable that the remaining rate after collagenase treatment at a collagenase concentration of 0.25%, a temperature of 37 °C, and pH 7.4 for a reaction time of 15 minutes be 80% or more, and it is even more preferable that the remaining rate after collagenase treatment at a collagenase concentration of 0.25%, a temperature of 37 °C, and pH 7.4 for a reaction time of 15 minutes be 90% or more. Such a three-dimensional tissue is less likely to undergo decomposition by an enzyme in culture or after culture, thus being stable.

It is preferable that the thickness of the three-dimensional tissue be 10 μm or more, it is more preferable that the thickness of the three-dimensional tissue be 100 μm or more, and it is even more preferable that the thickness of the three-dimensional tissue be 1000 μm or more. Such a three-dimensional tissue has a structure closer to that of biological tissue, thus being preferred as an alternative to experimental animals and transplantation materials. The upper limit of the thickness of the three-dimensional tissue is not limited, and may be, for example, 10 mm or less, 3 mm or less, 2 mm or less, 1.5 mm or less, or 1 mm or less.

The "thickness of the three-dimensional tissue" indicates, if the three-dimensional tissue has a sheet-like or rectangular parallelepiped shape, the distance between two ends in the direction perpendicular to the principal surface. If the principal surface has unevenness, the thickness indicates the distance at the thinnest part of the principal surface.

If the three-dimensional tissue has a spherical or nearly spherical shape, the thickness indicates the diameter. If the three-dimensional tissue has an ellipsoidal or nearly ellipsoidal shape, the thickness indicates the minor axis. If the three-dimensional tissue has a nearly spherical or nearly ellipsoidal shape and the surface has unevenness, the thickness indicates the shortest distance among distances between two points of intersection of a line passing through the center of gravity of the three-dimensional tissue and the surface.

The Young's modulus of the three-dimensional tissue may be that at 10 °C to 45 °C, it is preferable that the Young's modulus of the three-dimensional tissue be that at 15 °C to 40°, it is more preferable that the Young's modulus of the three-dimensional tissue be that at 20 °C to 37 °C, and it is further preferable that the Young's modulus of the three-dimensional tissue be that at 25 °C (±1 °C).

According to the method of the present embodiment, a three-dimensional tissue having a desired Young's modulus can be obtained, and hence the Young's modulus of the three-dimensional tissue is not limited; for example, the Young's modulus of the three-dimensional tissue may be 20 kPa to 300 kPa, 20 kPa to 250 kPa, 30 kPa to 150 kPa, 40 kPa to 100 kPa, 50 kPa to 80 kPa, or 50 kPa to 70 kPa. The Young's modulus of the three-dimensional tissue may be, for example, 150 kPa or more, 200 kPa or more, or 250 kPa or more, but is not limited thereto.

The Young's modulus of the three-dimensional tissue can be measured by using the compact tabletop tester EZ-test (manufactured by Shimadzu Corporation). Specifically, gel (or a three-dimensional tissue) mounted on a common culture vessel is compressed with a rod-like jig (tip area: 11 $mm^2$) set on a load cell of the tester at a temperature of 25 °C and a compression rate of 1.0 mm/min to obtain a stress-strain curve. The Young's modulus (kPa) can be calculated from the slope in an elastic region at the beginning of stress increase in the stress-strain curve obtained.

<Method for Producing Three-Dimensional Tissue>

The method of the present embodiment for producing a three-dimensional tissue comprises: a step of providing a fragmented extracellular matrix subjected to adjustment of average diameter according to a desired Young's modulus for the three-dimensional tissue; a step of obtaining a cell suspension by mixing the extracellular matrix and cells in an aqueous medium; and a step of incubating the cell suspension.

(Step of Providing Fragmented Extracellular Matrix)

The production method of the present embodiment comprises a step of providing a fragmented extracellular matrix subjected to adjustment of average diameter according to a desired Young's modulus for the three-dimensional tissue.

The three-dimensional tissue, Young's modulus, fragmented extracellular matrix, method for adjusting the average diameter, and others are as described above. The production method of the present embodiment may comprise a step of adjusting the average diameter of the fragmented extracellular matrix.

The average diameter of the fragmented extracellular matrix may be, for example, 20 nm or more and 30 μm or less, or 20 nm or more and 10 μm or less. In the production method of the present embodiment, the Young's modulus of the three-dimensional tissue can be increased by decreasing the average diameter of the fragmented extracellular matrix contained in the three-dimensional tissue; conversely, the Young's modulus of the three-dimensional tissue can be decreased by increasing the average diameter. Accordingly, the fragmented extracellular matrix subjected to adjustment of average diameter in the production method of the present embodiment may contain a fragmented extracellular matrix whose average diameter has been adjusted to any of average diameters shown as examples in the following.

The fragmented extracellular matrix subjected to adjustment of average diameter may be nanofiber. The average diameter of the nanofiber may be, for example, 20 nm or more and 1000 nm or less, 20 nm or more and 500 nm or less, 20 nm or more and 200 nm or less, 40 nm or more and 130 nm or less, or 20 nm or more and 100 nm or less. The fragmented extracellular matrix subjected to adjustment of average diameter may be microfiber. The average diameter of the microfiber may be, for example, more than 1 μm and 30 μm or less, more than 1 μm and 30 μm or less, more than 1 μm and 10 μm or less, 1.5 μm or more and 8.5 μm or less, or 2 μm or more and 8.5 μm or less.

In the production method of the present embodiment, the fragmented extracellular matrix subjected to adjustment of average diameter may be totally nanofiber or microfiber. The fragmented extracellular matrix subjected to adjustment of average diameter may contain fragmented extracellular matrices having different average diameters. For example, both the aforementioned nanofiber and microfiber may be contained; specifically, for example, a fragmented extracellular matrix of 20 nm or more and 1000 nm or less and a fragmented extracellular matrix having an average diameter of 1.5 μm or more and 8.5 μm or less may be contained. Nanofibers having different average diameters may be contained; specifically, for example, a fragmented extracellular matrix of 20 nm or more and 100 nm or less and a fragmented extracellular matrix of more than 100 nm and 200 nm or less may be contained. A desired Young's modulus can be imparted to the three-dimensional tissue by adjusting the ratio of the fragmented extracellular matrices having different average diameters in terms of weight. For example, the fragmented extracellular matrix of smaller average diameter (e.g., nanofiber) and the fragmented extracellular matrix of larger average diameter (e.g., microfiber) may be used at a ratio of 1:100 to 100:1, at a ratio of 1:10 to 10:1, at a ratio of 1:3 to 3:1, or at a ratio of 1:2 to 2:1, in terms of weight. Specifically, for example, a fragmented extracellular matrix having an average diameter of 20 nm or more and 1000 nm or less and a fragmented extracellular matrix having an average diameter of 1.5 μm or more and 8.5 μm or less can be used at a ratio of 1:100 to 100:1 in terms of weight. The fragmented extracellular matrix of smaller average diameter (e.g., nanofiber) may be used more than the fragmented extracellular matrix of larger average diameter (e.g., microfiber) in terms of weight. Specifically, for example, a fragmented extracellular matrix having an average diameter of 20 nm or more and 1000 nm or less may be used more than a fragmented extracellular matrix having an average diameter of 1.5 μm or more and 8.5 μm or less in terms of weight.

In the production method of the present embodiment, the Young's modulus of the three-dimensional tissue may be controlled by adjusting the average diameter and content percentage of the fragmented extracellular matrix. Accordingly, the step of providing a fragmented extracellular matrix in the production method of the present embodiment may be a step of providing a fragmented extracellular matrix subjected to adjustment of average diameter and content according to a desired Young's modulus for the three-dimensional tissue. For example, the Young's modulus of the three-dimensional tissue can be increased by increasing the content of the fragmented extracellular matrix of small average diameter in the three-dimensional tissue or decreasing the content of the fragmented extracellular matrix of large average diameter in the three-dimensional tissue. Conversely, the Young's modulus of the three-dimensional tissue can be decreased by decreasing the content of the fragmented extracellular matrix of small average diameter in the three-dimensional tissue or increasing the content of the fragmented extracellular matrix of large average diameter in the three-dimensional tissue. That is, adjusting the three-dimensional tissue to contain fragmented extracellular matrices having different average diameters and adjusting the contents of the fragmented extracellular matrices having different average diameters in the three-dimensional tissue may include increasing the Young's modulus of the three-dimensional tissue by increasing the content of the fragmented extracellular matrix of small average diameter in the three-dimensional tissue, or decreasing the Young's modulus of the three-dimensional tissue by decreasing the content of the fragmented extracellular matrix of small average diameter in the three-dimensional tissue. The production method of the present embodiment may further include a step of mixing the provided fragmented extracellular matrices having different average diameters. The cells may be added after mixing the fragmented extracellular matrices having different average diameters, or mixed together with the fragmented extracellular matrices having different average diameters.

The content percentage of the fragmented extracellular matrix to be used in the production method of the present embodiment may be 0.33% by mass or more, 0.5% by mass or more, 1% by mass or more, 2% by mass or more, or 5% by weight or more, on the basis of the total mass of the fragmented extracellular matrix and the cells. The content of the fragmented extracellular matrix in the three-dimensional tissue may be, for example, 90% by mass or less, 80% by mass or less, 70% by mass or less, 60% by mass or less, 50% by mass or less, 40% by mass or less, 30% by mass or less, 20% by mass or less, 15% by mass or less, 10% by mass or less, 5% by mass or less, or 1% by mass or less, on the basis of the total mass of the extracellular matrix subjected to fragmentation and the cells. The content of the fragmented extracellular matrix in the three-dimensional tissue may be, for example, 0.33% by mass or more and 90% by mass or less, or 0.5% by mass or more and 90% by mass or less, or 1.0% by mass or more and 90% by mass or less, or 5% by weight or more and 90% by weight or less, or 5% by weight or more and 40% by weight or less, on the basis of the total mass of the extracellular matrix subjected to fragmentation and the cells.

The extracellular matrix subjected to fragmentation can be obtained with the above-described method. The extracellular matrix subjected to fragmentation may be one obtained by fragmenting an extracellular matrix in an aqueous medium. That is, the production method according to the present embodiment may comprise a step of fragmenting an extracellular matrix in an aqueous medium (fragmentation step) in the step of providing a fragmented extracellular matrix.

The extracellular matrix subjected to fragmentation may be any of those shown above as examples, and may contain collagen subjected to fragmentation.

The production method according to the present embodiment may further include a step of crosslinking at least part of an extracellular matrix by heating the extracellular matrix before the fragmentation step, or include a step of crosslinking at least part of an extracellular matrix by heating the extracellular matrix after the fragmentation step and before the step of obtaining a cell suspension. In the step of crosslinking at least part of an extracellular matrix, a freeze-dried product of the extracellular matrix may be heated.

In the step of crosslinking, the temperature (heating temperature) and time (heating time) in heating the extracellular matrix can be appropriately determined. The heating temperature may be, for example, 100 °C or more, and 200 °C or less or 220 °C or less. Specifically, the heating temperature may be, for example, 100 °C, 110 °C, 120 °C, 130 °C, 140 °C, 150 °C, 160 °C, 170 °C, 180 °C, 190 °C, 200 °C, or 220 °C. The heating time (the time to keep at the heating temperature) can be appropriately set in view of the heating temperature. The heating time, for example, in heating at 100 °C to 200 °C may be 6 hours or more and 72 hours or less, and is more preferably 24 hours or more and 48 hours or less. In the step of crosslinking, heating may be performed in the absence of solvent, and heating may be performed under conditions with reduced pressure.

The production method according to the present embodiment may include a drying step of drying the extracellular matrix subjected to fragmentation after the fragmentation step.

In the drying step, the extracellular matrix subjected to defibering is dried. The drying may be carried out, for example, by a freeze-drying method. The aqueous medium is removed from the liquid containing the fragmented extracellular matrix component and the aqueous medium by performing the drying step after the defibering step. The statement that the aqueous medium is removed does not mean that moisture attaching to the extracellular matrix subjected to fragmentation is completely absent, but that attaching moisture is absent to a degree normally achievable by the aforementioned common drying technique.

(Step of Obtaining Cell Suspension)

The production method of the present embodiment comprises a step of obtaining a cell suspension by mixing the fragmented extracellular matrix and cells in an aqueous medium.

Dispersing the fragmented extracellular matrix in an aqueous medium can allow the fragmented extracellular matrix to readily come into contact with cells in the aqueous medium, promoting the formation of the three-dimensional tissue.

Examples of methods for mixing the fragmented extracellular matrix and the cells in an aqueous medium include a method of mixing an aqueous medium containing the fragmented extracellular matrix and an aqueous medium containing the cells, a method of adding the cells to an aqueous medium containing the fragmented extracellular matrix, a method of adding an aqueous medium containing the extracellular matrix to a culture solution containing the cells, a method of adding the cells to an aqueous medium containing the fragmented extracellular matrix, and a method of adding the extracellular matrix and the cells to an aqueous medium prepared previously, but are not limited to these methods. The fragmented extracellular matrix and the cells may be stirred in an aqueous medium by pipetting or the like.

In the method of adding the cells to an aqueous medium containing the fragmented extracellular matrix, the aqueous medium containing the fragmented extracellular matrix can be produced by dispersing the fragmented extracellular matrix in an aqueous medium. The aqueous medium for the cell culture composition may be the same as or different from the aqueous medium in mixing the extracellular matrix and the cells. If the aqueous media are the same, a cell suspension may be obtained by mixing the cells into the aqueous medium containing the fragmented extracellular matrix. If the aqueous media are different, the aqueous medium in the aqueous medium containing the fragmented extracellular matrix may be called the first aqueous medium, and the aqueous medium in mixing with the cells may be called the second aqueous medium.

A cell suspension can be obtained through the process that the fragmented extracellular matrix and the cells are dispersed in an aqueous medium. The aqueous medium may be a culture medium. The culture medium is not limited, and a preferred culture medium can be selected according to the type of cells to be cultured. Examples of the culture medium include the culture media Eagle's MEM, DMEM, Modified Eagle Medium (MEM), Minimum Essential Medium, RPMI, and GlutaMax. The culture medium may be a culture medium to which serum has been added, or a serum-free culture medium. The culture medium may be a mixed culture medium obtained by mixing two culture media.

The concentration of the extracellular matrix in the step of obtaining a cell suspension can be appropriately determined according to the Young's modulus, shape, and thickness to be achieved for the three-dimensional tissue, the size of an incubator, and so on. For example, the concentration of the extracellular matrix in the aqueous medium in the step of obtaining a cell suspension may be 0.1 to 90% by mass, or 1 to 30% by mass.

The amount of the fragmented extracellular matrix in the step of obtaining a cell suspension may be, for example, 0.1 to 100 mg, 0.5 to 50 mg, 0.8 to 25 mg, 1.0 to 10 mg, 1.0 to 5.0 mg, 1.0 to 2.0 mg, or 1.0 to 1.8 mg, or may be 0.7 mg or more, 1.1 mg or more, 1.2 mg or more, 1.3 mg or more, or 1.4 mg or more, and may be 7.0 mg or less, 3.0 mg or less, 2.3 mg or less, 1.8 mg or less, 1.7 mg or less, 1.6 mg or less, or 1.5 mg or less, per $1.0\times10^{6}$ cells.

In the step of obtaining a cell suspension, it is preferable that the mass ratio between the fragmented extracellular matrix and the cells (fragmented extracellular matrix/cells) be 1/1 to 1000/1, it is more preferable that the mass ratio between the fragmented extracellular matrix and the cells be 9/1 to 900/1, and it is further preferable that the mass ratio between the fragmented extracellular matrix and the cells be 10/1 to 500/1.

Adding fibrinogen and/or thrombin may be included in the step of obtaining a cell suspension, or after the step of obtaining a cell suspension and before the incubation step. If both fibrinogen and thrombin are added, for example, fibrinogen and thrombin may be simultaneously added, or addition of fibrinogen may be followed by addition of thrombin. The timing to add fibrinogen and/or thrombin is not limited; for example, fibrinogen and/or thrombin may be added to the aqueous medium containing the cells and the fragmented extracellular matrix, or addition of fibrinogen and subsequent addition of fat cells to the aqueous medium containing the cells and the fragmented extracellular matrix may be followed by addition of thrombin. Addition of fibrinogen and/or thrombin can prevent shrinkage that may occur in the incubation step described later, resulting in easiness in controlling the shape and size of the three-dimensional tissue. In addition, the suspension of the cells and the fragmented extracellular matrix can be gelled, which leads to easiness in peeling-off from an incubator (support) after dropping the suspension onto the incubator. If the cells include mature fat cells, the fat cells float under the influence of lipid droplets within the mature fat cells, and as a result the fat cells and other cells may be cultured in a heterogeneous state; however, gelling of the suspension allows the cells and the extracellular matrix to keep the homogeneously mixed state, and thus to readily keep a state in which the cells and the extracellular matrix are close to each other.

The production method of the present embodiment may comprise a step of accumulating the cells and the fragmented extracellular matrix by applying external force to the cell suspension after the step of obtaining a cell suspension and before the incubating the cell suspension. The distribution of the fragmented extracellular matrix and the cells in the three-dimensional tissue becomes more homogeneous by performing such a step. Examples of specific methods therefor include, but are not limited to, a method of centrifuging the cell suspension containing the extracellular matrix and the cells.

(Step of Incubating Cell Suspension)

The production method of the present embodiment comprises a step of incubating the cell suspension.

In the production method according to the present embodiment, the incubation step is a step of incubating the cells in contact with the extracellular matrix subjected to fragmentation. The cells in contact with the fragmented extracellular matrix can be cultured through incubation. Accordingly, the present step is occasionally referred to as the “culture step”.

The incubation method is not limited, and a preferred method can be performed according to the type of cells. For example, the incubation temperature may be 20 °C to 40 °C, or 30 °C to 37 °C. The pH of the cell suspension may be 6 to 8, or 7.2 to 7.4. The incubation time may be 1 day to 2 weeks, or 1 week to 2 weeks.

The incubator (support) to be used in incubating the cell suspension is not limited, and may be, for example, a well insert, a low adhesion plate, or a plate having a U-shaped, V-shaped, or otherwise shaped bottom. The cells may be cultured with the cells adhered to a support, or cultured without the cells adhered to a support, or cultured with peeling off the cells from a support in the middle of culture. If the cells are cultured without the cells adhered to a support, or cultured with peeling off the cells from a support in the middle of culture, it is preferable to use a plate having a U-shaped, V-shaped, or otherwise shaped bottom or a low adhesion plate, each of which inhibits the adhesion of the cells to the support.

The cell density in the culture medium in the culture step can be appropriately determined according to the shape and thickness to be achieved for the three-dimensional tissue, the size of an incubator, and so on. For example, the cell density in the culture medium in the culture step may be 1 to $10^8$ cells/mL, or $10^3$ to $10^7$ cells/mL. The cell density in the culture medium in the culture step may be the same as the cell density in the aqueous medium in the contact step.

It is preferable that the shrinkage percentage of the three-dimensional tissue to be produced with the production method according to the present embodiment in culture be 20% or less, it is more preferable that the shrinkage rate of the three-dimensional tissue to be produced with the production method according to the present embodiment in culture be 15% or less, and it is further preferable that the shrinkage rate of the three-dimensional tissue to be produced with the production method according to the present embodiment in culture be 10% or less. The shrinkage percentage can be calculated, for example, by an expression below. In the expression, Li denotes the length of the longest part of the three-dimensional tissue on day 1 of culture, and L3 denotes the length of the corresponding part of the three-dimensional tissue on day 3 of culture.

$$\text{Shrinkage percentage (\%)} = \{(L1 - L3\} \times 100$$

Although the shrinkage percentage is calculated from the three-dimensional tissue on day 1 of culture and the cell tissue on day 3 of culture in this example, the shrinkage percentage may be calculated from the three-dimensional tissue at any points of time in the culture period including the end point of culture. For example, the shrinkage percentage may be calculated from the three-dimensional tissue on day 1 of culture and from the three-dimensional tissue on day 2 of culture, or calculated from the three-dimensional tissue on day 1 of culture and from the three-dimensional tissue on day 5 of culture, or calculated from the three-dimensional tissue on day 1 of culture and from the three-dimensional tissue on day 8 of culture.

After the culture step (hereinafter, also referred to as the “first culture step”; the initial contact step is also referred to as the “first contact step”), a step of bringing cells into contact (second contact step) and a step of culturing cells (second culture step) may be further included. The cells in the second contact step and the second culture step may be of a type identical to or different from the type of the cells used in the first contact step and the first culture step. The second contact step and the second culture step allow a three-dimensional tissue of bilayer structure to be produced. Further, inclusion of repeated contact steps and culture steps allows a multilayered three-dimensional tissue to be produced, and thus enables production of more complex tissues close to biological ones.

The above culture step may include culturing the cells in contact with the extracellular matrix subjected to fragmentation without the cells adhered to a support. Thereby, a three-dimensional tissue as a massive assembly not adhering to a support can be produced. If the cells in contact with the extracellular matrix subjected to fragmentation is adhering to a support, the culture step may include peeling off the cells in contact with the extracellular matrix subjected to fragmentation from the support. If the cells in contact with the extracellular matrix subjected to fragmentation are not adhering to a support from the beginning of the culture step, a three-dimensional tissue as a massive assembly not adhering to a support can be produced by culturing the cells as they are.

The method for peeling off the cells in contact with the extracellular matrix subjected to fragmentation from a support is not limited; for example, the cells may be peeled off from a support in such a manner that a low adhesion support is used and a culture solution is additionally added to peel off the cells from the support, the cells may be physically peeled off from a support by means of an instrument or the like, the cells may be peeled off from a support by applying vibration, and the cells may be peeled off from a support in such a manner that a support the surface of which has been coated with a functional material that allows bonds between the support and cells to be broken in response to stimulation such as heat and light is used, and stimulation is applied to peel off the cells from the support. If the cells are peeled off from a support by additionally adding a culture solution, any of the culture media and the like shown above as examples can be used as the culture solution.

Examples of methods for culturing the cells in contact with the extracellular matrix subjected to fragmentation without the cells adhered to a support from the beginning of the culture step include, for example, a method of gelling the suspension containing the cells in contact with the extracellular matrix subjected to fragmentation and gently adding the resultant dropwise to a culture solution for culture, and a method of fixing the shape of the cells in contact with the extracellular matrix subjected to fragmentation to some extent in a solvent having high viscosity and then transferring the resultant to a culture vessel with only the solvent removed.

The timing to peel off the cells in contact with the extracellular matrix subjected to fragmentation from a support in the culture step is not limited, and peeling-off may be performed, for example, within 1 day to 7 days, or within 1 hour to 24 hours, or within 1 minute to 60 minutes, or within 5 minutes to 30 minutes, or within 10 minutes to 20 minutes, after the beginning of culture.

The culture period after the cells in contact with the extracellular matrix subjected to fragmentation were peeled off from a support is not limited, and may be 1 day or more, 1 day to 21 days, 3 days to 14 days, or 7 days to 14 days.

The Young's modulus of the three-dimensional tissue to be produced with the production method of the present embodiment may be that at 10 °C to 45 °C, it is preferable that the Young's modulus of the three-dimensional tissue to be produced with the production method of the present embodiment be that at 15 °C to 40°, it is more preferable that the Young's modulus of the three-dimensional tissue to be produced with the production method of the present embodiment be that at 20 °C to 37 °C, and it is further preferable that the Young's modulus of the three-dimensional tissue be that at 25 °C (±1 °C).

According to the production method of the present embodiment, a three-dimensional tissue having a desired Young's modulus can be obtained, and hence the Young's modulus of the three-dimensional tissue is not limited; for example, the Young's modulus of the three-dimensional tissue may be 1 kPa or more, or 5 kPa or more, or 10 kPa or more, or 20 kPa or more, or 40 kPa or more, or 50 kPa or more, or 75 kPa or more, or 100 kPa or more, or 150 kPa or more, or 20 kPa to 250 kPa, or 30 kPa to 150 kPa, or 40 kPa to 100 kPa, or 50 kPa to 80 kPa, or 50 kPa to 70 kPa.

The above-described specific modes or the like can be applied to specific modes or the like of the production method of the present embodiment, without limitation.

<Three-Dimensional Tissue>

An embodiment of the present invention can provide a three-dimensional tissue, comprising: cells; and a fragmented extracellular matrix having an average diameter of 20 nm or more and 1000 nm or less, wherein the fragmented extracellular matrix is disposed among at least some of the cells, the fragmented extracellular matrix is a biocompatible material with molecules identical to biomolecules, and the three-dimensional tissue has a Young's modulus of 20 kPa or more.

The fragmented extracellular matrix, measurement of the Young's modulus, and so on are as described above.

The Young's modulus of the three-dimensional tissue of the present embodiment is 20 kPa or more, and may be 40 kPa or more, 50 kPa or more, 75 kPa or more, 100 kPa or more, 150 kPa or more, 200 kPa or more, or 250 kPa or more. The Young's modulus may be 10 kPa to 300 kPa, or 10 kPa to 250 kPa, or 20 kPa to 150 kPa, or 30 kPa to 100 kPa.

The content percentage of the fragmented extracellular matrix may be, for example, 0.33% by mass or more and 90% by mass or less, or 0.5% by mass or more and 90% by mass or less, or 1.0% by mass or more and 90% by mass or less, or 5% by weight or more and 90% by weight or less, or 5% by weight or more and 40% by weight or less, on the basis of the total mass of the three-dimensional tissue.

The three-dimensional tissue of the present embodiment may further contain a fragmented extracellular matrix having an average diameter of more than 1000 nm, for example, a fragmented extracellular matrix having an average diameter of 1.5 μm or more and 8.5 μm or less. If a fragmented extracellular matrix having an average diameter of more than 1000 nm (e.g., a fragmented extracellular matrix having an average diameter of 1.5 μm or more and 8.5 μm or less) is contained, the fragmented extracellular matrix having an average diameter of 20 nm or more and 1000 nm or less and the fragmented extracellular matrix having an average diameter of more than 1000 nm (e.g., a fragmented extracellular matrix having an average diameter of 1.5 μm or more and 8.5 μm or less) may be used at a ratio of 1:100 to 100:1 in terms of weight.

The above-described specific modes or the like can be applied to specific modes or the like of the three-dimensional tissue of the present embodiment, without limitation.

<Forming Agent for Three-Dimensional Tissue>

An embodiment of the present invention can provide a forming agent for a three-dimensional tissue, comprising: a fragmented extracellular matrix having an average diameter of 20 nm or more and 1000 nm or less; and an aqueous medium, wherein the three-dimensional tissue has a Young's modulus of 20 kPa or more.

The three-dimensional tissue, the fragmented extracellular matrix, the aqueous medium, measurement of the Young's modulus, and so on are as described above.

The forming agent for a three-dimensional tissue of the present embodiment can be used for formation of a three-dimensional tissue having a Young's modulus of 20 kPa or more. A three-dimensional tissue may be produced by obtaining a cell suspension by mixing the forming agent for a three-dimensional tissue and cells and incubating the cell suspension.

The Young's modulus of the three-dimensional tissue may be 1 kPa or more, 5 kPa or more, 10 kPa or more, 20 kPa or more, 40 kPa or more, 50 kPa or more, 75 kPa or more, 100 kPa or more, 150 kPa or more, 200 kPa or more, or 250 kPa or more. The Young's modulus may be 10 kPa to 300 kPa, 10 kPa to 250 kPa, 20 kPa to 150 kPa, or 30 kPa to 100 kPa.

The Young's modulus of the forming agent of the present embodiment for a three-dimensional tissue can be measured in the same manner as for the three-dimensional tissue, and may be 20 kPa or more, 40 kPa or more, 50 kPa or more, 75 kPa or more, 100 kPa or more, 200 kPa or more, or 250 kPa or more. The Young's modulus may be 10 kPa to 300 kPa, 10 kPa to 200 kPa, 20 kPa to 150 kPa, or 30 kPa to 100 kPa. The Young's modulus may be that at 10 °C to 45 °C, it is preferable that the Young's modulus be that at 15 °C to 40 °C, it is more preferable that the Young's modulus be that at 20 °C to 37 °C, and it is further preferable that the Young's modulus be that at 25 °C (±1 °C).

Inclusion of the aforementioned fragmented extracellular matrix having an average diameter of 20 nm or more and 1000 nm or less and aqueous medium allows a cell culture composition having a Young's modulus of 20 kPa or more at 25 °C (±1 °C) to be produced. The method for providing the fragmented extracellular matrix having an average diameter of 20 nm or more and 1000 nm or less is as described above.

The content percentage of the fragmented extracellular matrix may be 0.33% by mass or more and 90% by mass or less, or 0.5% by mass or more and 90% by mass or less, or 1.0% by mass or more and 90% by mass or less, or 5% by weight or more and 90% by weight or less, or 5% by weight or more and 40% by weight or less, on the basis of the total mass of the forming agent for a three-dimensional tissue.

The above-described specific modes or the like can be applied to specific modes or the like of the forming agent of the present embodiment.

EXAMPLES

Example 1: Purification of Type I Collagen

To 500 mL of ultrapure water, 1 g of porcine skin-derived type I and type III mixed collagen manufactured by NH Foods Ltd. was added, and the resultant was incubated at 4 °C for 12 hours to produce 0.2% by weight collagen solution. Thereafter, 0.45 M NaCl and 5 mM Tris-HCl were added to the collagen solution, which was incubated at 4 °C for 12 hours, and then further incubated at 4 °C for 12 hours with addition of 1.2 M NaCl. After incubation, centrifugation was performed at 10000 rpm for 15 minutes, and the supernatant was collected, giving purified type I collagen solution.

The type I collagen solution obtained was dialyzed (molecular weight cutoff (MWCO): 15 kDa) with ultrapure water for 7 days, and then freeze-dried for 3 days, giving purified type I collagen.

Example 2: Preparation and Fiber Diameter Evaluation of Collagen Microfiber and Collagen Nanofiber In 5 mL of 1×PBS (pH=7.4), 50 mg of the purified type I collagen obtained in Example 1 was suspended, and homogenization was performed with a stirring homogenizer at room temperature for 6 minutes to give a dispersion containing fragmented collagen. FIG. 1 shows a graph representing the fiber diameter distribution of the fragmented collagen in the dispersion. The average diameter of the fragmented collagen obtained was 5.03±3.11 μm (number of samples: 25). Hereinafter, the fragmented collagen is also referred to as collagen microfiber (CMF).

Figure 2:
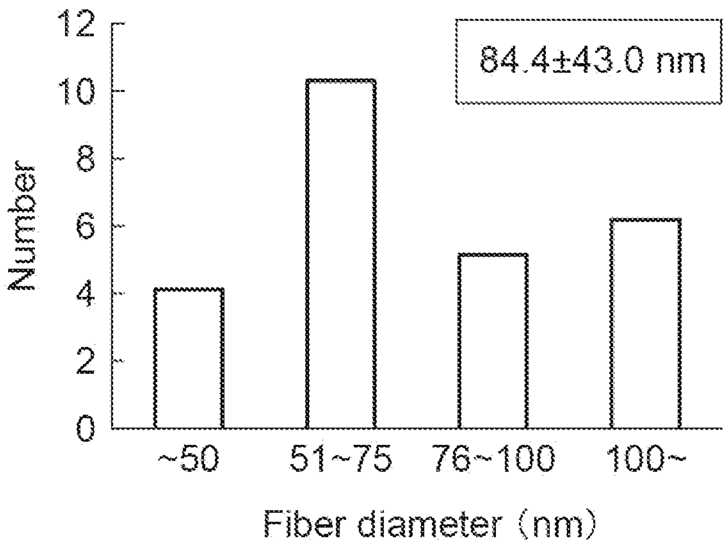
FIG. 2 shows a graph representing the fiber diameter distribution of fragmented collagen in a collagen solution in Example 2.

In 5 mL of 1×PBS (pH=7.4), 50 mg of the purified type I collagen obtained in Example 1 was suspended, homogenization was performed with a stirring homogenizer at room temperature for 6 minutes, and then incubation was further performed at 4 °C for 3 days, resulting in the formation of finer fragmented collagen. FIG. 2 shows a graph representing the fiber diameter distribution of the fragmented collagen in the solution. The average diameter of the fragmented collagen obtained was 84.4±43.0 nm (number of samples: 25). Hereinafter, the fragmented collagen is also referred to as collagen nanofiber (CNF).

Example 3: Production of Gel Using Collagen Nanofiber and Evaluation of Young's Modulus CNF-containing liquids, produced with the same method as in Example 2 to give specific concentrations (0.1 to 3.0% by weight), were added dropwise into a 24-Transwell at 300 μL/well, and incubation was further performed at 37 °C for 3 hours for gelation to give CNF gels of about 8 to 9 mm in thickness.

For comparison, 0.1% by weight collagen gel (Nippi gel) was produced with an acid solution of porcine skin-derived type I collagen manufactured by Nippi, Incorporated in accordance with a protocol provided by the manufacturer.

The Young's modulus of the gels were measured at 25 °C in the following manner.

Measurement was performed by using the compact tabletop tester EZ-test (manufactured by Shimadzu Corporation). Specifically, gel mounted on a 24-well insert (manufactured by Corning Incorporated) was compressed with a rod-like jig (tip area: 11 $mm^2$) set on a load cell of the tester at a temperature of 25 °C and a compression rate of 1.0 mm/min to obtain a stress-strain curve. The Young's modulus (kPa) was calculated from the slope in an elastic region at the beginning of stress increase in the stress-strain curve obtained.

Figure 3:
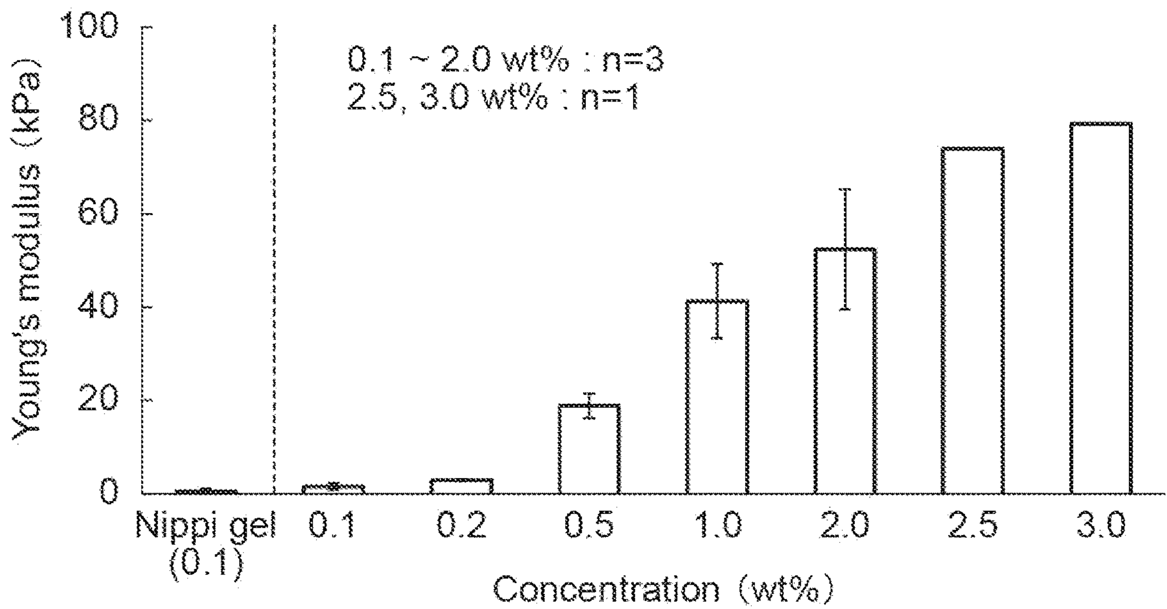
FIG. 3 shows a graph representing the variation of the Young's modulus of CNF gel against CNF concentration in Example 3.

FIG. 3 shows the results. It was demonstrated that the Young's modulus of CNF can be increased by increasing the concentration (% by weight) of CNF. Even a gel having a Young's modulus 160 times as much as that of the commercially available Nippi gel was successfully produced.

Example 4: Production of Gel Using Collagen Microfiber and Comparison of Young's Modulus CMF-containing liquids, produced with the same method as in Example 2 to give specific concentrations (0.2 to 2.0% by weight), were added dropwise into a 24-Transwell at 300 μL/well, and incubation was further performed at 37 °C for 3 hours for gelation to give CMF gels of about 8 to 9 mm in thickness. The Young's modulus of the CMF gels at 25 °C were compared with the Young's modulus of the CNF gels produced in Example 3.

Figure 4:
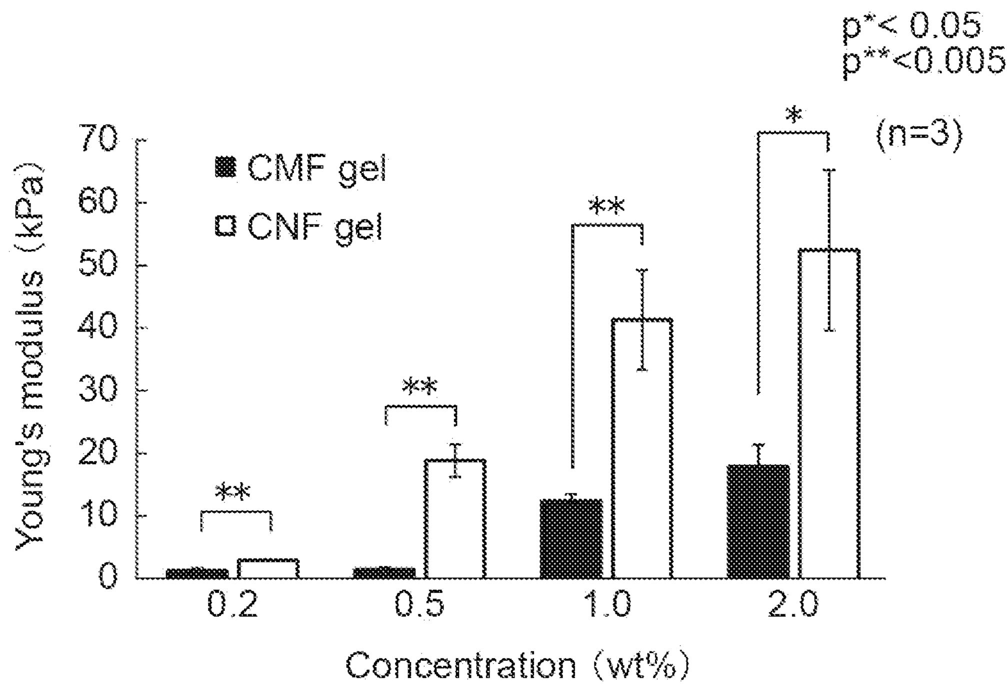
FIG. 4 shows a graph representing results of comparison of the Young's modulus of CNF gel and CMF gel in Example 4.

FIG. 4 shows the results. The CNF gels exhibited higher Young's modulus than the CMF gels at the same concentration. The transmittance (500 nm) of the 1% by weight CNF gel was 0.12(%), which was higher than the transmittance (500 nm) of the CMF gel at the same concentration, 0.03(%).

Example 5: Production of Three-Dimensional Tissue Bodies Using Collagen Microfiber and Comparison of Young's Modulus Three-dimensional tissue bodies were produced with the collagen microfiber (CMF) and collagen nanofiber (CNF) produced in Example 2 in the following manner.

First, CMF and/or CNF was dispersed in DMEM to prepare 2 wt % CNF dispersion, 1 wt % CNF dispersion, 0.5% CNF dispersion, 1.33 wt % CNF+0.66% CMF dispersion, and 0.66 wt % CNF+1.33% CMF dispersion.

A human colorectal adenocarcinoma cell line (HT29) (ATCC number: CCL-247) subcultured in a 10 cm dish by a conventional method was peeled off from the 10 cm dish and collected. HT29 was suspended in each of the dispersions to reach $1\times10^6$ cells per 400 μL, giving cell suspensions.

To a deep well plate (manufactured by Caplugs Evergreen, #222-8636-010), 400 μL of each cell suspension was seeded. Incubation was performed at 37 °C, and the Young's modulus of three-dimensional tissue bodies 1 day after seeding were measured at 25 °C in the same manner as in Examples 3 and 4.

Figure 5:
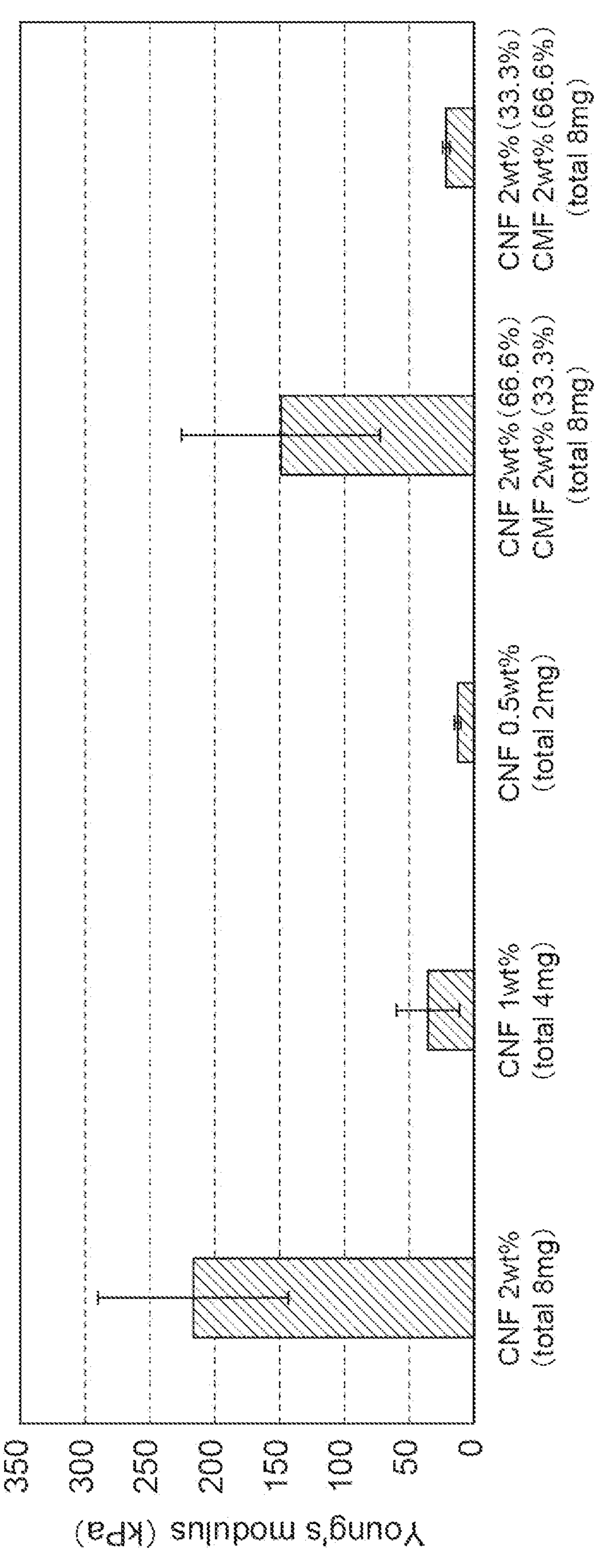
FIG. 5 shows a graph representing results of comparison of the Young's modulus of three-dimensional tissue bodies in Example 5.

FIG. 5 shows the results. The notations (total 2 mg), (total 4 mg), and (total 8 mg) in FIG. 5 each indicate the total amount of fragmented collagen (CMF and/or CNF) contained in a three-dimensional tissue formed. The calculation was on the assumption that the specific gravity of each cell suspension was 1 mg per 1 μL. In the graph of FIG. 5, the first to third from the left show the results of culture of cell suspensions obtained by mixing a CNF dispersion and HT29 to give a final concentration of CNF of 2 wt %, 1 wt %, or 0.5 wt %. The fourth from the left shows that 2 wt % CNF dispersion and 2 wt % CMF dispersion were mixed at volume percentages of 66.6% and 33.3%, respectively. That is, it shows the result of culture of a cell suspension containing CNF and CMF at a ratio of 66.6:33.3 (approximately 1.3 wt %: approximately 0.7 wt %). The fifth from the left shows that 2 wt % CNF dispersion and 2 wt % CMF dispersion were mixed at volume percentages of 33.3% and 66.6%, respectively. That is, it shows the result of culture of a cell suspension containing CNF and CMF at a ratio of 33.3:66.6 (approximately 0.7 wt %: approximately 1.3 wt %).

These demonstrated that mixing of fragmented collagens having different fiber diameters gives difference in hardness (Young's modulus) depending on the mixing ratio among three-dimensional tissue bodies to be produced, even with the same total amount of fragmented collagens. Specifically, it was found that when a three-dimensional tissue containing CNF and CMF is produced, the Young's modulus is enhanced by increasing the ratio of CNF, which has small fiber length, and conversely the Young's modulus decreases by increasing the ratio of CMF, which has large fiber length, even with the same total amount of fragmented collagens (comparison of the first, fourth, and fifth from the left in FIG. 5). In addition, it was demonstrated that inclusion of 2 wt % or more of CNF allows a three-dimensional tissue having a Young's modulus of 200 kPa or more to be produced (the first from the left in FIG. 5), and that inclusion of approximately 1.3 wt % or more of CNF allows a three-dimensional tissue having a Young's modulus of 100 kPa or more to be produced (the fourth from the left in FIG. 5). Moreover, the three-dimensional tissue bodies produced were each a three-dimensional tissue in which collagen was three-dimensionally disposed among cells, and cells and collagen were homogeneously distributed.

The invention claimed is:

1. A method for controlling a Young's modulus of a three-dimensional tissue containing cells and an extracellular matrix, comprising altering an average diameter of a fragmented extracellular matrix to produce the three-dimensional tissue, wherein the fragmented extracellular matrix consists of collagen;

the altering an average diameter of the fragmented extracellular matrix includes altering the three-dimensional tissue to contain fragmented extracellular matrices having different average diameters while keeping a total concentration of the collagen constant, the fragmented extracellular matrices having different average diameters include a fragmented extracellular matrix having an average diameter in a range of 20 nm to 1000 nm and a fragmented extracellular matrix having an average diameter in a range of 1000 nm to 30 μm.

2. The method according to claim 1, wherein the altering the three-dimensional tissue to contain fragmented extracellular matrices having different average diameters in the three-dimensional tissue include:

increasing the Young's modulus of the three-dimensional tissue by increasing the content of a fragmented extracellular matrix having the average diameter in a range of 20 nm to 1000 nm in the three-dimensional tissue, or decreasing the Young's modulus of the three-dimensional tissue by decreasing the content of a fragmented extracellular matrix having the average diameter in a range of 20 nm to 1000 nm in the three-dimensional tissue.

3. The method according to claim 1, wherein the fragmented extracellular matrix having the average diameter in the range of 1000 nm to 30 um has an average diameter in between 1.5 um and 8.5 um.

4. The method according to claim 3, wherein the Young's modulus of the three-dimensional tissue is 100 kPa or more, and wherein the fragmented extracellular matrix having the average diameter in a range of 20 nm to 1000 nm has an average diameter between 40 nm and 130 nm and has the content of 1.3 weight % or more.

5. The method according to claim 4, wherein the Young's modulus of the three-dimensional tissue is 200 kPa or more, and wherein the content of the fragmented extracellular matrix having the average diameter between 40 nm and 130 nm is 2.0 weight % or more.

6. The method according to claim 1, wherein the fragmented extracellular matrix having the average diameter in a range of 20 nm to 1000 nm and the fragmented extracellular matrix having the average diameter in a range of 1000 nm to 30 um are used at a ratio of 1:100 to 100:1 in terms of weight.

7. The method according to claim 1, wherein the Young's modulus of the three-dimensional tissue is 20 kPa to 250 kPa.

* * * * *